United States Patent
Omi (10) Patent No.: US 10,016,176 B2
(45) Date of Patent: Jul. 10, 2018

(54) X-RAY IMAGE PROCESSING APPARATUS AND METHOD, AND X-RAY IMAGING APPARATUS

(71) Applicant: CANON KABUSHIKI KAISHA, Tokyo (JP)

(72) Inventor: Hiroyuki Omi, Kamakura (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 77 days.

(21) Appl. No.: 15/025,450

(22) PCT Filed: Sep. 29, 2014

(86) PCT No.: PCT/JP2014/004962
§ 371 (c)(1),
(2) Date: May 24, 2016

(87) PCT Pub. No.: WO2015/052890
PCT Pub. Date: Apr. 16, 2015

(65) Prior Publication Data
US 2016/0270752 A1  Sep. 22, 2016

(30) Foreign Application Priority Data

Oct. 10, 2013  (JP) .................................. 2013-213224

(51) Int. Cl.
*A61B 6/00* (2006.01)
*G06T 5/00* (2006.01)
(Continued)

(52) U.S. Cl.
CPC ............ *A61B 6/5211* (2013.01); *A61B 6/486* (2013.01); *A61B 6/487* (2013.01); *A61B 6/5235* (2013.01);
(Continued)

(58) Field of Classification Search
None
See application file for complete search history.

(56) References Cited

U.S. PATENT DOCUMENTS

| 5,675,624 A * | 10/1997 | Relihan | H04N 5/32 348/E5.086 |
| 2013/0112874 A1* | 5/2013 | Osvath | A61B 6/486 250/311 |

(Continued)

FOREIGN PATENT DOCUMENTS

| JP | S63-92336 A | 4/1988 |
| JP | H01-212983 A | 8/1989 |

(Continued)

OTHER PUBLICATIONS

Translation of the JPO Notification of Reasons for Refusal Application No. 2013-213224 (Foreign Priority Document of the present Application), Published Jun. 29, 2017.*

(Continued)

*Primary Examiner* — Kim Vu
*Assistant Examiner* — Nathan Bloom
(74) *Attorney, Agent, or Firm* — Carter, DeLuca, Farrell & Schmidt, LLP (57) ABSTRACT

An X-ray image processing apparatus for performing image processing for frames successively obtained by an X-ray sensor acquires a first analysis value and a second analysis value by analyzing each of the successively obtained frames, and calculates, as a first statistic and a second statistic, statistics in a time direction of the first analysis values and the second analysis values of the successively obtained frames. Based on the calculated first and second statistics, the X-ray image processing apparatus determines whether to correct the first analysis value. If it is determined to correct (Continued)

the first analysis value, the X-ray image processing apparatus corrects the first analysis value based on the first statistic.

27 Claims, 9 Drawing Sheets

(51) Int. Cl.
    *G06T 5/20* (2006.01)
    *G06T 5/50* (2006.01)
    *G06T 7/00* (2017.01)

(52) U.S. Cl.
    CPC ............ *A61B 6/5258* (2013.01); *G06T 5/007* (2013.01); *G06T 5/20* (2013.01); *G06T 5/50* (2013.01); *G06T 7/0012* (2013.01); *G06T 2207/10116* (2013.01); *G06T 2207/20021* (2013.01); *G06T 2207/20182* (2013.01); *G06T 2207/30004* (2013.01)

(56) References Cited

U.S. PATENT DOCUMENTS

2013/0201198 A1* 8/2013 Nagatsuka ............. A61B 6/463
    345/581

2014/0093043 A1* 4/2014 Nakatsugawa ........ A61B 6/481
    378/62

FOREIGN PATENT DOCUMENTS

| | | |
|---|---|---|
| JP | H04-139587 A | 5/1992 |
| JP | H05-49143 B | 7/1993 |
| JP | H06-268915 A | 9/1994 |
| JP | H07-240886 A | 9/1995 |
| JP | H08-77329 A | 3/1996 |
| JP | 2009-033293 A | 2/2009 |
| JP | 2011-125462 A | 6/2011 |
| JP | 2013-127773 A | 6/2013 |

OTHER PUBLICATIONS

Translation of the Written Opinion of the International Searching Authority for PCT/JP2014/004962 (PCT Document of the Present Application), dated Dec. 22, 2014.*

PCT International Search Report and Written Opinion of the International Searching Authority dated Dec. 22, 2014.

* cited by examiner

WHEN R1(5) HAS SUCCEEDED

| ID | 1 | 2 | 3 | 4 |
|---|---|---|---|---|
| R1(t) | 2100 | 2122 | 2111 | 2132 |
| FRAME NUMBER t | 4 | 3 | 2 | 1 |

→

| ID | 1 | 2 | 3 | 4 |
|---|---|---|---|---|
| R1(t) | 2130 | 2100 | 2122 | 2111 |
| FRAME NUMBER t | 5 | 4 | 3 | 2 |

FIG. 4B

WHEN R1(5) HAS FAILED

| ID | 1 | 2 | 3 | 4 |
|---|---|---|---|---|
| R1(t) | 2100 | 2122 | 2111 | 2132 |
| FRAME NUMBER t | 4 | 3 | 2 | 1 |

→

| ID | 1 | 2 | 3 | 4 |
|---|---|---|---|---|
| R1(t) | 2100 | 2122 | 2111 | 2132 |
| FRAME NUMBER t | 4 | 3 | 2 | 1 |

FIG. 4C

WHEN R1(10) HAS FAILED

| ID | 1 | 2 | 3 | 4 |
|---|---|---|---|---|
| R1(t) | 2100 | 2122 | 2111 | 2132 |
| FRAME NUMBER t | 4 | 3 | 2 | 1 |

→

| ID | 1 | 2 | 3 | 4 |
|---|---|---|---|---|
| R1(t) | 1988 | 2100 | 2122 | 2111 |
| FRAME NUMBER t | 10 | 4 | 3 | 2 |

X-RAY IMAGE PROCESSING APPARATUS AND METHOD, AND X-RAY IMAGING APPARATUS

This application is a continuation of International Patent Application No. PCT/JP2014/004962 filed on Sep. 29, 2014, and claims priority to Japanese Patent Application No. 2013-213224 filed on Oct. 10, 2013, the entire content of both of which is incorporated herein by reference.

TECHNICAL FIELD

The present invention relates to an X-ray image processing apparatus and method for performing tone processing for an X-ray image, an X-ray imaging apparatus.

BACKGROUND ART

In general, to hold given image quality of an X-ray image output from a sensor, an X-ray fluoroscopic system monitors the dose of X-rays which have reached the sensor, and controls the incident dose to make the value of the X-ray dose constant. If the dose which has reached the sensor is low, an instruction to increase the incident dose is issued, and if the dose which has reached the sensor is high, an instruction to decrease the incident dose is issued, thereby controlling the irradiation amount of X-rays. In this specification, control of the dose will be referred to as automatic dose control (ADC) hereinafter.

If fluoroscopic images of the same object are continuously obtained by successively capturing X-ray images, the fluoroscopic images of the object are continuously obtained with a constant dose after optimizing the irradiation amount of X-rays by ADC. This state will be referred to as a state in which "ADC is stable" hereinafter. In the state in which ADC is stable, the tone of an X-ray image observed by the user remains unchanged, and an image free from any luminance fluctuation is displayed.

Since, however, an X-ray generation apparatus cannot output a completely constant dose, an output which fluctuates to some extent is generally obtained. As a result, even though fluoroscopic images of the same object are continuously obtained, the luminance of an X-ray image observed by the user may fluctuate. To cope with this, the X-ray image is optimized by further performing image processing for the image obtained by optimization by ADC, thereby suppressing luminance fluctuations. For example, an input image is analyzed to create a tone conversion curve so that a region of interest always has a constant luminance value, and a result of processing the image using the created tone conversion curve is output as a final image.

To generate an optimum tone conversion curve for suppressing fluctuations of the X-ray generation apparatus, it is necessary to perform image analysis to determine the state of the X-ray image. In such image analysis, an object region is extracted by extracting a collimation region and direct irradiated region (region where X-rays directly enter) from the X-ray image, and an analysis value for setting an optimum tone of the extracted object region is calculated. By improving the analysis accuracy, it is possible to output a more optimum final image.

However, as the analysis accuracy improves, processing becomes more difficult, resulting in an increase in probability that image analysis fails. If image analysis fails, it is impossible to obtain an optimum tone conversion curve, so an image having an inappropriate luminance is output. If fluoroscopic images of the same object are continuously obtained, a frame for which image analysis has failed has an inappropriate luminance, and the user feels that flicker has occurred.

As a method of correcting the influence of flicker, there is provided a method of reducing the influence of a failed analysis value by smoothing, in a time-axis direction, analysis values calculated by image analysis (PTL 1). As another method, there is provided a method of analyzing an image to calculate an analysis value, and adding, to the analysis value, a difference value between the analysis value and an analysis value obtained by smoothing in a time-axis direction (PTL 2). A value for stabilization is calculated by smoothing in the time direction, and a value is made to match the calculated value, thereby eliminating flicker.

CITATION LIST

Patent Literature

PTL 1: Japanese Patent Laid-Open No. 1-212983
PTL 2: Japanese Patent Laid-Open No. 2009-33293
PTL 3: Japanese examined Patent Publication No. 05-049143

SUMMARY OF INVENTION

Technical Problem

In the method described in PTL 1, it is possible to reduce the influence of flicker by smoothing. However, if a failure amount is large, the reduction effect weakens, and flicker unwantedly occurs. In the method described in PTL 2 as well, since there are fluctuations of an X-ray generation apparatus, an analysis value also fluctuates. Furthermore, if an average value is used as a correction value with respect to a value for which it is determined that image analysis has failed, it is impossible to consider fluctuations of the X-ray generation apparatus, and a luminance unwantedly fluctuates.

Solution to Problem

An X-ray image processing apparatus according to one aspect of the present invention has the following arrangement. That is, there is provided an X-ray image processing apparatus for performing image processing for frames successively obtained by an X-ray sensor, comprising: an analysis unit configured to obtain a first analysis value and a second analysis value by analyzing each of the successively obtained frames; a calculation unit configured to calculate, as a first statistic and a second statistic, statistics in a time direction of the first analysis values and the second analysis values of the successively obtained frames; a determination unit configured to determine, based on the first statistic and the second statistic, whether to correct the first analysis value; and a correction unit configured to, if the determination unit determines to correct the first analysis value, correct the first analysis value based on the first statistic.

Advantageous Effects of Invention

According to the present invention, even if the irradiation amount of X-rays fluctuates, it is possible to effectively suppress flicker.

Other features and advantages of the present invention will be apparent from the following description taken in conjunction with the accompanying drawings. Note that the same reference numerals denote the same or like components throughout the accompanying drawings.

BRIEF DESCRIPTION OF DRAWINGS

The accompanying drawings, which are incorporated in and constitute a part of the specification, illustrate exemplary embodiments of the invention and, together with the description, serve to explain the principles of the present invention.

DESCRIPTION OF EMBODIMENTS

Preferred embodiments of the present invention will be exemplified below with reference to the accompanying drawings.

First Embodiment

Figure 1:
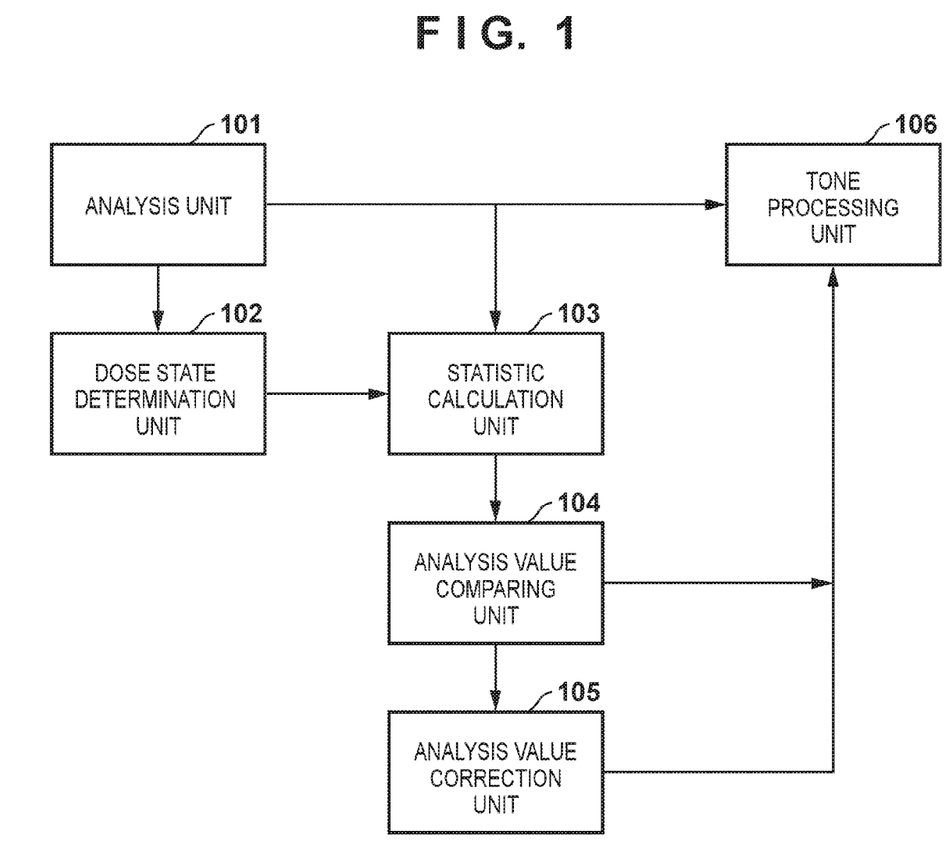
FIG. 1 is a block diagram showing an example of the functional arrangement of an X-ray image processing apparatus according to an embodiment.

FIG. 1 shows an example of a functional arrangement for implementing an X-ray image processing method for an X-ray imaging apparatus according to the first embodiment. According to this embodiment, even if the irradiation amount of X-rays fluctuates, it is possible to effectively suppress flicker. The X-ray image processing method according to this embodiment is implemented by an X-ray image processing apparatus including an analysis unit 101, a dose state determination unit 102, a statistic calculation unit 103, an analysis value comparing unit 104, an analysis value correction unit 105, and a tone processing unit 106.

The analysis unit 101 receives an image (to be referred to as a preprocessed image hereinafter) obtained by performing predetermined preprocessing for an X-ray image acquired by an X-ray sensor, and outputs an analysis value to be used for tone processing. The preprocessing is processing of correcting the characteristics of the sensor such as offset correction, gain correction, or defect correction, and processing of setting a state in which the correlation with peripheral pixels is maintained. The dose state determination unit 102 receives the analysis value output from the analysis unit 101, and outputs a result of determining whether ADC is stable. The statistic calculation unit 103 receives the analysis value from the analysis unit 101 and the determination result from the dose state determination unit 102, and calculates the statistic in the time direction of the analysis values. The analysis value comparing unit 104 receives the statistic in the time direction, which has been calculated by the statistic calculation unit 103, and determines whether the analysis value is an appropriate value. The analysis value correction unit 105 outputs a result of correcting the analysis value to an appropriate value when the analysis value comparing unit 104 determines that the analysis value is not an appropriate value. The tone processing unit 106 performs tone processing for the preprocessed image using the analysis value output from the analysis unit 101 or the corrected analysis value output from the analysis value correction unit 105. Note that based on the determination result of the analysis value comparing unit 104, the tone processing unit 106 determines whether to use the corrected analysis value.

Figure 2:
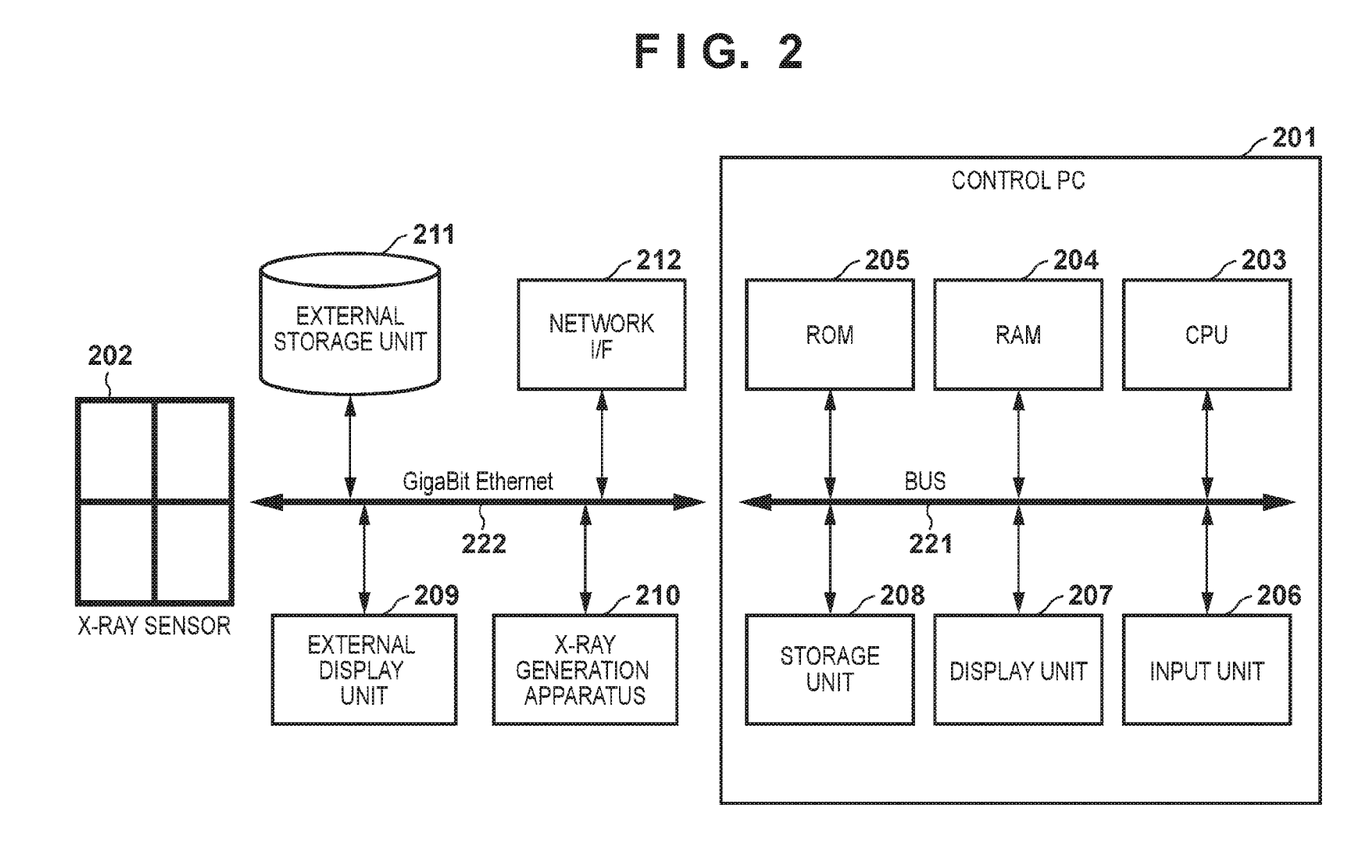
FIG. 2 is a block diagram showing an example of the hardware arrangement of the X-ray image processing apparatus.

When the arrangement shown in FIG. 1 is implemented using an information processing apparatus (to be referred to as a control PC hereinafter) such as a computer, an example of a hardware arrangement is as shown in FIG. 2. A control PC 201, an X-ray sensor 202 serving as an X-ray detection panel, and an X-ray generation apparatus 210 are connected by GigaBit Ethernet 222. Note that a signal line is not limited to GigaBit Ethernet, and may be CAN (Controller Area Network), an optical fiber, or the like. The X-ray sensor 202 outputs an electrical signal corresponding to an X-ray dose, and the output electrical signal is stored in an external storage unit 211 as, for example, an X-ray image.

An external display unit 209, the external storage unit 211, and a network interface unit 212 are connected to the GigaBit Ethernet 222. In the control PC 201, for example, a CPU (Central Processing Unit) 203, a RAM (Random Access Memory) 204, a ROM (Read Only Memory) 205, an input unit 206, a display unit 207, and a storage unit 208 are connected to a bus 221. Commands are sent to the X-ray sensor 202, the external display unit 209, and the like via the control PC 201. In the control PC 201, processing contents for each imaging mode are stored in the storage unit 208 as a software module, and the software module is loaded into the RAM 204, and executed by the CPU 203. Each component shown in FIG. 1 is stored in the storage unit 208 as a software module. Each component shown in FIG. 1 may be mounted as a dedicated image processing board, as a matter of course, and is optimally implemented according to the purpose. The X-ray image processing method according to the first embodiment will be described in detail below.

In this embodiment, an X-ray fluoroscopic system will be exemplified as an X-ray imaging apparatus. X-ray image processing in the X-ray fluoroscopic system according to the first embodiment will be described with reference to the block diagram of FIG. 1 and the flowchart of FIG. 3. In the X-ray image processing according to this embodiment, image processing (tone processing in this embodiment) is performed for frames (preprocessed X-ray images) successively obtained from the X-ray sensor 202. The analysis unit 101 analyzes each of the successively obtained frames, and outputs a plurality of analysis values including analysis values 1 and 2 (to be described later). Note that the preprocessed image is stored in, for example, the external storage unit 211, and read out by the analysis unit 101 or the tone processing unit 106.

Figure 3:
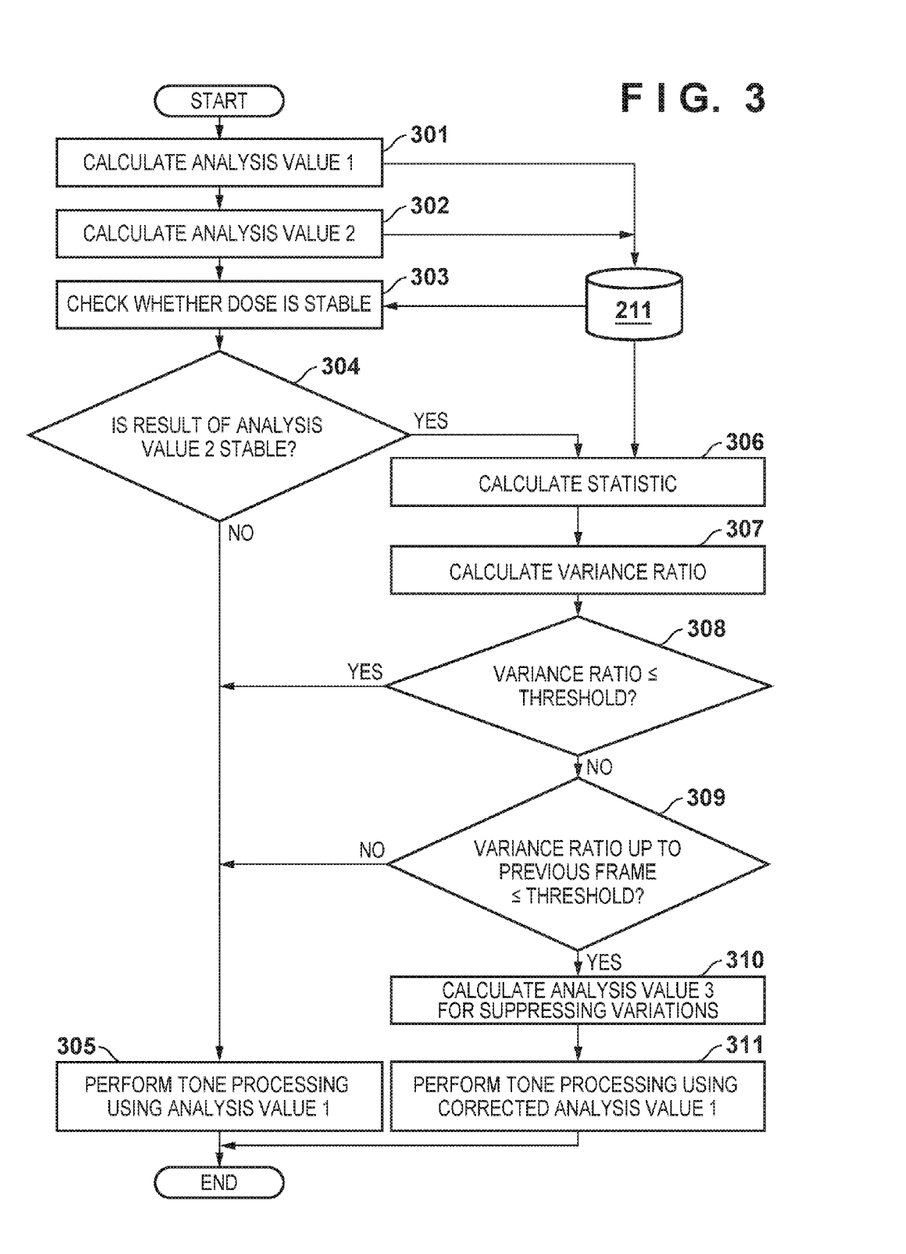
FIG. 3 is a flowchart illustrating processing of acquiring analysis values for tone processing.

The analysis unit 101 according to this embodiment calculates analysis values 1 and 2 by performing analysis processing for different regions of one frame. First, the analysis unit 101 outputs, as analysis value 1, a value representing the pixel values of an object region from the preprocessed image (step 301). There are various methods of extracting an object region, and any known method may be used. For example, it is possible to extract an object region by extracting a collimation region and direct irradiated region from the image.

For example, the method described in PTL 3 is used to extract a collimation region. This method sets an X- and Y-axes along two adjacent sides of the outline of a rectangular irradiation field, and adds and totals image data in the set X-axis direction and Y-axis direction. The value of the added/totaled data within the irradiation field is higher than that of a region, outside the irradiation field, which is hardly irradiated with X-rays. Consequently, a position on the Y-axis at which the value of the added/totaled data in the X-axis direction is equal to or higher than a predetermined threshold TH and a position on the X-axis at which the value of the added/totaled data in the Y-axis direction is equal to or higher than the predetermined threshold TH are calculated. Then, a rectangular region surrounded by a straight line in the X-axis direction on the calculated position on the Y-axis and a straight line in the Y-axis direction at the calculated position on the X-axis is set as a collimation region.

The direct irradiated region indicates a region where emitted X-rays directly reach the sensor without passing through the object. If, for example, an image histogram is calculated, the direct irradiated region concentrates in a high-pixel value region. Therefore, it is possible to extract <eliminate> the direct irradiated region by eliminating several % from the high-pixel value side of the histogram range. Note that a collimation region extraction method and a direct irradiated region extraction method are not limited to them.

A region obtained by eliminating the thus obtained collimation region and direct irradiated region from the X-ray image is set as an object region. As a value representing the object region, for example, the average value, intermediate value, or the like of the object region can be used. Calculated analysis value 1 is saved in, for example, the external storage unit 211. Note that an image to be processed by the analysis unit 101 is a preprocessed image. However, an image having undergone processing such as log conversion, emphasis processing, or noise suppression processing instead of preprocessing may be input.

The analysis unit 101 calculates, from the preprocessed image, analysis value 2 to be used for ADC (step 302). The analysis value to be used for ADC is calculated by a simpler method than that for analysis value 1 to reduce the risk of an analysis failure. For example, a representative value of a region of a predetermined size at a predetermined position in the preprocessed image is used. In this embodiment, the average value of a region of a several-inch square at the center of the preprocessed image is calculated as analysis value 2. Calculated analysis values 1 and 2 are saved in the external storage unit 211 in association with, for example, a frame number.

The dose state determination unit 102 calculates a statistic in the time direction with respect to analysis values 2 of the successively obtained frames, and determines whether the X-ray dose is stable. More specifically, the dose state determination unit 102 inputs analysis value 2 of the current frame and analysis values 2 calculated for past frames from the external storage unit 211, and performs statistical processing for the analysis values. Based on a statistic obtained by the statistical processing, it is determined whether ADC is stable or not (steps 303 and 304). In this example, the variance or standard deviation of analysis values 2 can be used as a statistic. When ADC works, analysis value 2 varies. Therefore, the variation amount of analysis value 2 is calculated to perform threshold processing. Let $R_2(t)$ be the value of analysis value 2, and t be a frame number. Then, as an index representing the variation amount, the variance $V_2(t)$ is calculated by:

$$V_2(t) = \frac{1}{n_2 - 1} \sum_{k=0}^{n_2 - 1} (R_2(t-k) - \overline{R_2})^2 \quad (1)$$

$$\overline{R_2} = \frac{1}{n_2} \sum_{k=0}^{n_2 - 1} R_2(t-k)$$

where $n_2$ represents a sampling count in the time direction.

If the value of the variance $V_2(t)$ does not exceed a threshold, it is determined that no X-ray control is performed, and then determined that ADC is stable. If it is determined that ADC is unstable, it is difficult to determine whether analysis value 1 has succeeded or failed, and thus analysis value 1 is not corrected. That is, the tone processing unit 106 performs tone processing for the preprocessed image using analysis value 1 which has not been corrected (step 305).

On the other hand, if it is determined that ADC is stable, the statistic calculation unit 103 and analysis value comparing unit 104 determine whether to execute correction processing of analysis value 1. To perform this determination processing, the statistic calculation unit 103 calculates the statistic in the time direction of analysis values 1 of the successively obtained frames. That is, the statistic calculation unit 103 reads out analysis value 1 of the current frame and the results of analysis values 1 calculated for the past frames from the external storage unit 211, and calculates a statistic for determining whether analysis value 1 of the current frame has succeeded or failed (step 306). The variance or standard deviation can be used as the statistic, similarly to analysis value 2. In this embodiment, the variance $V_1(t)$ in the time direction of analysis values 1 is calculated as the statistic by equations (2) where $R_1(t)$ represents the value of analysis value 1, t represents a frame number, and $n_1$ represents a sampling count in the time direction.

$$V_1(t) = \frac{1}{n_1 - 1} \sum_{k=0}^{n_1 - 1} (R_1(t-k) - \overline{R_1})^2 \quad (2)$$

$$\overline{R_1} = \frac{1}{n_1} \sum_{k=0}^{n_1 - 1} R_1(t-k)$$

The analysis value comparing unit 104 receives the variance $V_1(t)$ of analysis values 1 and the variance $V_2(t)$ of analysis values 2, and determines whether analysis value 1 has failed (steps 307 and 308). To perform this determination processing, the analysis value comparing unit 104 calculates a variance ratio by dividing $V_1(t)$ by $V_2(t)$, and compares the calculated ratio with a threshold. If ADC is stable and analysis value 1 has not failed, the variances $V_1(t)$ and $V_2(t)$ are almost equal to each other. Therefore, if the variance ratio is equal to or smaller than the threshold, it is determined that analysis value 1 is correct. If it is determined that analysis value 1 is correct, the tone processing unit 106 uses analysis value 1 without performing correction to perform tone processing for the preprocessed image (step 305).

If it is determined, as a result of comparison in step 308, that analysis value 1 has failed (acquisition of analysis value 1 has failed), correction of analysis value 1 may be executed in step 310. Since, however, it is impossible to determine an analysis value which has failed among sampled analysis values 1, if analysis values 1 are simply corrected according to the result in step 308, analysis value 1 which need not be corrected may be corrected. To cope with this, in this embodiment, it is confirmed whether acquisition of analysis value 1 of the current frame has failed, by referring to a predetermined number of past frames (step 309). With this confirmation processing, it can be correctly determined whether it is necessary to execute correction of analysis value 1 of the current frame. Note that if a failure of analysis value 1 of the current frame cannot be confirmed in step 309, correction of analysis value 1 is prohibited, and analysis value 1 is directly used. The confirmation processing according to this embodiment will be described below.

If the variance ratio exceeds the threshold while ADC is stable, the analysis values used to calculate the variance $V_1(t)$ include a failed analysis value. In this embodiment, to clarify that analysis of a target frame has failed, it is confirmed that the variance ratio up to the previous frame is equal to or smaller than the threshold (step 309). If the variance ratio up to the previous frame is equal to or smaller than the threshold but the threshold of the variance ratio is exceeded by newly added analysis value 1 of the current frame, the failed analysis is analysis of the current frame. If the variance ratio up to the previous frame exceeds the threshold, a frame in which analysis has failed cannot be determined. Thus, the tone processing unit 106 performs tone processing for the preprocessed image using analysis values 1 without performing correction (step 305).

If the variance ratio up to the previous frame is equal to or smaller than the threshold, the analysis value correction unit 105 receives analysis values 1, their variance $V_1(t)$, and the variance $V_2(t)$ of analysis values 2, and outputs analysis value 3 obtained by correcting analysis value 1 (step 310). In this embodiment, the analysis value correction unit 105 corrects analysis value 1 using equations (3) so that the variance ratio including analysis value 1 of the current frame becomes equal to or smaller than a threshold thF. When analysis value 3 is represented by $R_3(t)$, a quadratic equation of $R_3(t)$ is solved.

$$\frac{V_1(t)}{V_2(t)} = thF \qquad (3)$$

$$\frac{1}{n_1 - 1} \cdot \left( (R_3(t) - \overline{R}_1)^2 + (R_1(t-k) - \overline{R}_1)^2 + \right.$$
$$\left. \ldots + (R_1(t - (n_1 - 1)) - \overline{R}_1)^2 \right) = thF \cdot V_2(t)$$

$$(1 - 1/n_1) \cdot R_3^2(t) - 2BR_3(t) + (A - n_1 B^2) = (n_1 - 1) \cdot thF \cdot V_2(t)$$

$$R_3(t) = \frac{B \pm \sqrt{B^2 - (1 - 1/n_1) \cdot (A - n_1 B^2 - (n_1 - 1) \cdot thF \cdot V_2(t))}}{(1 - 1/n_1)}$$

$$A = \sum_{i=1}^{t-1} R_1^2(i), \; B = \frac{1}{n} \sum_{i=1}^{t-1} R_1(i)$$

According to equations (3), when a solution is a real number, two results $R_{31}(t)$ and $R_{32}(t)$ are obtained. As a method of selecting one of the two obtained results, for example, a solution having a smallest difference with respect to analysis value 1 before correction is selected as an analysis value after correction. This processing is indicated by steps 6011, 6012, and 6013 of FIG. 6A. That is, the absolute value of the difference between $R_1(t)$ and each of $R_{31}(t)$ and $R_{32}(t)$ is calculated (step 6011), and one of $R_{31}(t)$ and $R_{32}(t)$, which has a smaller difference, is selected (inequalities (4), steps 6012 and S6013). By selecting one of $R_{31}(t)$ and $R_{32}(t)$, which is closer to $R_1(t)$, over-correction of the value of $R_1(t)$ is prevented.

$$|R_{31}(t) - R_1(t)| \leq |R_{32}(t) - R_1(t)| \ldots R_3(t) = R_{31}(t)$$

$$|R_{31}(t) - R_1(t)| > |R_{32}(t) - R_1(t)| \ldots R_3(t) = R_{32}(t) \qquad (4)$$

On the other hand, if the solution is an imaginary number, a value which makes the variance ratio closest to the threshold, that is, a value which minimizes the variance ratio is recalculated. To minimize the variance ratio, the minimum value of the quadratic equation is obtained. Since the third one of equations (3) has a downward-convex shape, the derivative value of the equation is calculated.

$$2(1 - 1/n_1) \cdot R_3(t) - 2B = 0 \qquad (5)$$

$$R_3(t) = \frac{B}{(1 - 1/n_1)}$$

As described above, according to the first embodiment, analysis value 1 is corrected so as to hold the variance ratio of analysis values 1 and 2 obtained from two different regions. Even if, therefore, variations of analysis values include fluctuations of the X-ray generation apparatus, it is possible to perform correction to hold the fluctuation components. As a result, it is possible to effectively suppress flicker. If the stability of the state of an X-ray dose is confirmed based on analysis values 2 calculated for the respective frames, it is determined whether it is necessary to correct analysis value 1. Therefore, even if the irradiation amount of X-rays fluctuates to some extent, it is possible to effectively suppress flicker. After that, the tone processing unit 106 performs tone processing for the preprocessed image using analysis value 3 (step 311). Note that an image to be processed by the tone processing unit 106 is a preprocessed image. However, an image having undergone processing such as emphasis processing or noise suppression processing instead of preprocessing may be used.

Note that in the above embodiment, the ratio between $V_1(t)$ and $V_2(t)$ is used. Since, however, it is confirmed that the X-ray dose is stable ($V_2(t)$ is equal to or smaller than the threshold), analysis value 1 may be corrected so that $V_1(t)$ becomes equal to a predetermined value. That is, if the dose state determination unit 102 determines based on the statistic of analysis values 2 that the X-ray dose is stable, determination of whether it is necessary to correct analysis value 1 and calculation of correction value of analysis value 1 may be executed based on the statistic of analysis values 1.

According to this embodiment, there is provided an X-ray image processing apparatus for performing image processing for frames successively obtained by an X-ray sensor, comprising an analysis unit (for example, the analysis unit 101) configured to obtain a first analysis value and a second analysis value by analyzing each of the successively obtained frames, a calculation unit (for example, the statistic calculation unit 103) configured to calculate, as a first statistic and a second statistic, statistics in a time direction of the first analysis values and the second analysis values of the successively obtained frames, a determination unit (for example, the dose state determination unit 102) configured to determine, based on the first statistic and the second statistic, whether to correct the first analysis value, and a correction unit (for example, the analysis value correction unit 105) configured to, if the determination unit determines to correct the first analysis value, correct the first analysis value based on the first statistic. Therefore, even if the irradiation amount of X-rays fluctuates, it is possible to effectively suppress flicker.

Note that the present invention can also be implemented by an X-ray image processing apparatus for performing image processing for frames successively obtained by an X-ray sensor, comprising an analysis unit (for example, the analysis unit 101) configured to obtain an analysis value by analyzing each of the successively obtained frames, a calculation unit (for example, the statistic calculation unit 103) configured to calculate a statistic in a time direction of the analysis values of the successively obtained frames, and a correction unit (for example, the analysis value correction unit 105) configured to correct the analysis value based on the statistic.

Second Embodiment

In the above first embodiment, processing when analysis value 1 of the current frame has failed has been described. In the second embodiment, processing for a next frame when it is determined that analysis value 1 of a previous frame has failed will be described with reference to the block diagram of FIG. 1 and the flowchart of FIG. 3. Note that in this embodiment, an external storage unit 211 is used as a holding unit for holding a predetermined number of past frames. Processes in steps 301 to 306 are the same as those up to the previous frame and the same as in the first embodiment, and a description thereof will be omitted.

An analysis value comparing unit 104 receives a variance $V_1(t)$ of analysis values 1 and a variance $V_2(t)$ of analysis values 2, and determines whether analysis value 1 has failed (steps 307 and 308). To perform this determination processing, the analysis value comparing unit 104 calculates a variance ratio by dividing $V_2(t)$ by $V_1(t)$, and compares the variance ratio with a threshold. If the variance ratio exceeds the threshold while ADC is stable, the analysis values used to calculate the variance $V_1(t)$ include a failed analysis value. To clarify that analysis of a target frame has failed, it is confirmed that the variance value up to the previous frame held in the holding unit is equal to or smaller than the threshold (step 309). In the second embodiment, when calculating the variance value up to the previous frame in step 309, the variance value is calculated without using analysis value 1 of the frame for which it is determined that analysis value 1 has failed. That is, in step 309, the variance value is calculated using analysis values 1 for which analysis has succeeded.

Figure 4A:
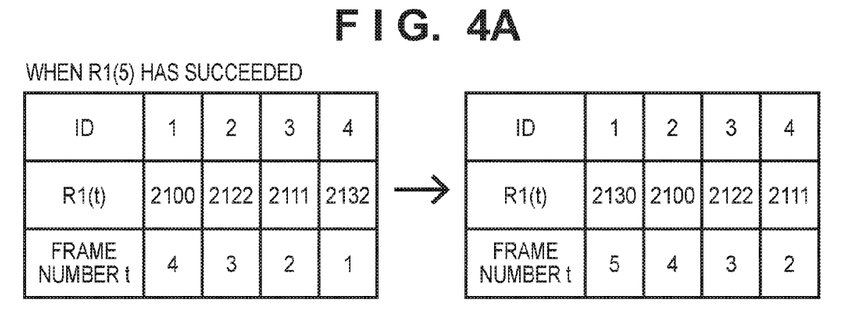
FIG. 4A is a view for explaining analysis value saving processing.
Figure 4B:
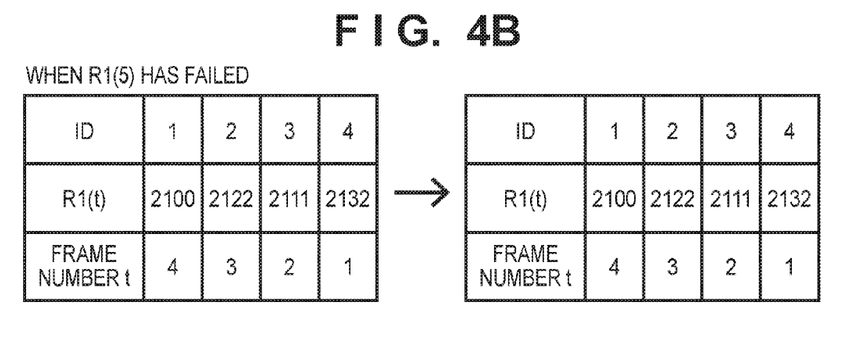
FIG. 4B is a view for explaining the analysis value saving processing.
Figure 4C:
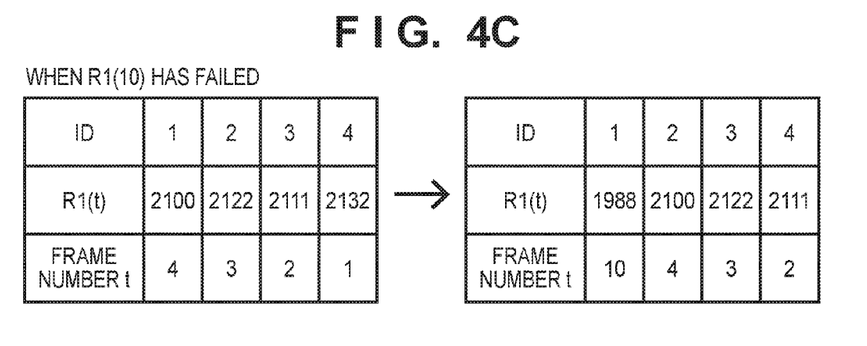
FIG. 4C is a view for explaining the analysis value saving processing.

FIGS. 4A to 4C show a method of selecting analysis values 1 calculated in past frames. FIGS. 4A to 4C are views each showing the storage status of the holding unit of the external storage unit 211 when a sample count is 4. The holding unit stores a value $R_1(t)$ of analysis value 1 at a frame number t, and holds analysis values 1 of past four frames. FIG. 4A is a view for explaining an operation of holding analysis value 1 in the holding unit when it is determined that analysis value 1 has succeeded for t=5. In this case, the oldest value of $R_1(1)$ is discarded, and the value of $R_1(5)$ is newly stored. This is done because it is desirable to perform comparison with the latest variance state and thus the oldest value is discarded. When t=6, $R_1(6)$ is determined based on these four values.

On the other hand, FIG. 4B is a view showing the storage status of the holding unit when it is determined that analysis value 1 has failed for t=5. In this case, the value of $R_1(5)$ is not stored in the holding unit. If failed analysis value 1 is used, it becomes impossible to clarify that analysis of the target frame has failed. However, if analysis value 1 continues to fail, the old variance values are unwantedly maintained in the holding unit forever. If, for example, the variance value gradually changes due to a trend component, determination cannot be correctly performed. Therefore, if the held contents of the holding unit are not updated for a predetermined number of frames (the number of frames from the frame of oldest analysis value 1 to the current frame exceeds the predetermined number of frames), the held contents of the holding unit are forcibly updated by analysis value 1 of the current frame.

FIG. 4C is a view for explaining the storage status of the holding unit when the threshold (the above-described predetermined number of frames) is 9. Since $R_1(10)$ is a failed analysis value but the threshold (9 frames) is exceeded, the oldest value of $R_1(1)$ is forcibly discarded and the value of $R_1(10)$ is stored. At this time, the variance value up to the previous frame is equal to or larger than the threshold, the analysis value $R_1$ is not corrected. In this way, if analysis value 1 of a past frame has failed, determination is performed without using the value.

Note that old analysis value 1 is discarded in this embodiment. However, if there is a sufficient memory capacity, the analysis value may be not discarded but held. As a selection method, a method of selecting a new value may be adopted. Processes in steps 310 and 311 are the same as in the first embodiment. In calculation of a variance ratio in step 307, failed analysis value 1 is not excluded. However, similarly to step 309, a variance ratio may be calculated by excluding failed analysis value 1.

In the second embodiment, in processing (step 309) of determining whether analysis value 1 of the current frame has failed, analysis value 1 which has been determined as a failed analysis value in the past is not used. The present invention, however, is not limited to this. For example, in step 306, the statistic calculation unit 103 may calculate a statistic by excluding, from analysis values 1 of past frames, an analysis value for which it is determined that correction is necessary (analysis value 1 determined as a failed analysis value)

Third Embodiment

Figure 6A:
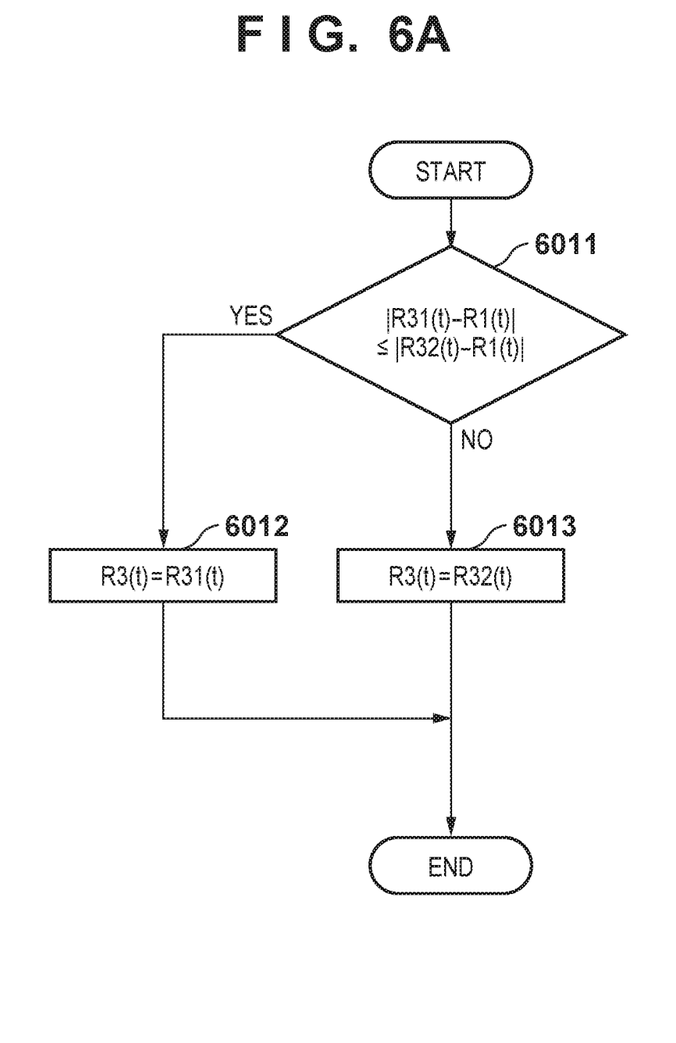
FIG. 6A is a flowchart for explaining a solution selection procedure.

In the first embodiment, when the solution of the quadratic equation of analysis value 3 is a real number, the method shown in FIG. 6A has been exemplified as a method of selecting one solution. The present invention is not limited to this. In the third embodiment, a modification of the solution selection method will be described. In the third embodiment, a solution is selected by the following processing.

(1) Among a plurality of solutions, a solution which makes the sign of the derivative value in the time direction of analysis values 1 match the sign of the derivative value in the time direction of analysis values 2 is selected as analysis value 1 after correction.

(2) Among a plurality of solutions with the same derivative value in the time direction of analysis values 1, a solution which minimizes the difference between the derivative value in the time direction of analysis values 1 and that of analysis values 2 is selected as analysis value 1 after correction. Detailed description thereof will be provided below.

In step 310, an analysis value correction unit 105 receives analysis values 1, their variance $V_1(t)$, and a variance $V_2(t)$ of analysis values 2, and generates analysis value 3 by correcting analysis value 1 determined as a failed analysis value. As described in the first embodiment, a method of correcting analysis value 1 uses equations (3) so that a variance ratio becomes equal to or smaller than a threshold thF. When the solution is a real number, two solutions ($R_{31}(t)$ and $R_{32}(t)$) are obtained, and it is thus necessary to select one of the two solutions. In this embodiment, a solution is selected according to a procedure shown in FIG. 6B.

Figure 6B:
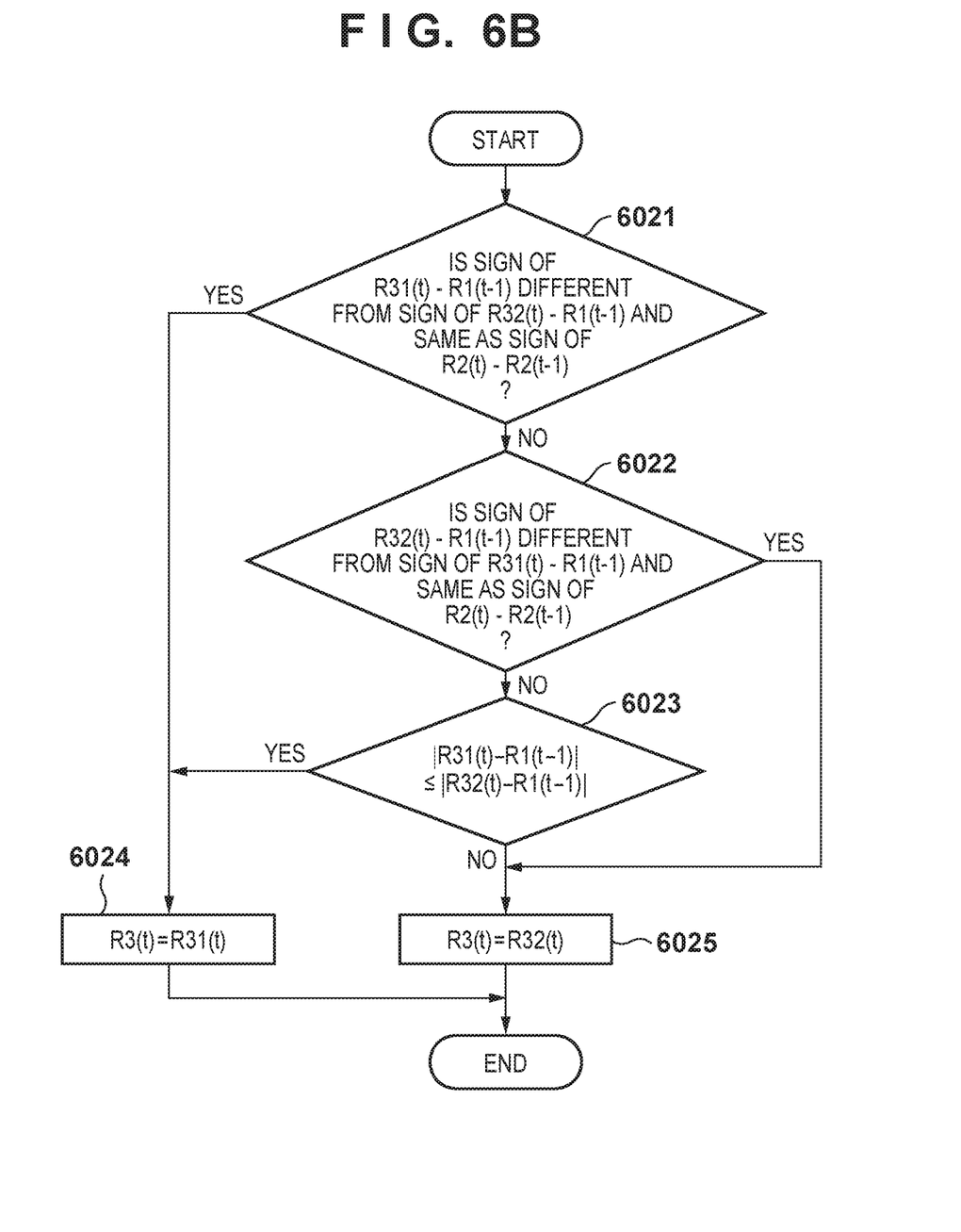
FIG. 6B is a flowchart for explaining a solution selection procedure.

Since a main factor of a variance is variations of an X-ray generation apparatus, the sign ($R_{31}(t)-R_1(t-1)$ or $R_{32}(t)-R_1(t-1)$) of the derivative value in the time direction of analysis values 1 and the sign of the derivative value ($R_2(t)-R_2(t-1)$) in the time direction of analysis values 2 are equal to each other. Therefore, one of the two solutions, which makes the sign of the derivative value equal to that of the derivative value of analysis values 2, is selected (steps 6021 and 6022). If the signs of the derivative values of the two solutions are equal to each other, selection is made by focusing attention on the magnitudes of the derivative values. That is, when a luminance difference and contrast difference with respect to the previous frame are large, the user recognizes flicker. Therefore, a solution having a smaller derivative value is selected (steps 6023, 6024, 6025), as given by $$|R_{31}(t)-R_3(t-1)| \le |R_{32}(t)-R_3(t-1)| \ldots R_3(t)=R_{31}(t)$$

$$|R_{31}(t)-R_3(t-1)| > |R_{32}(t)-R_3(t-1)| \ldots R_3(t)=R_{32}(t) \quad (6)$$

Note that the analysis value used for tone processing of a frame t−1 is not a corrected analysis value, $R_3(t-1)$ of inequalities (6) is equal to $R_1(t-1)$.

Fourth Embodiment

Figure 5:
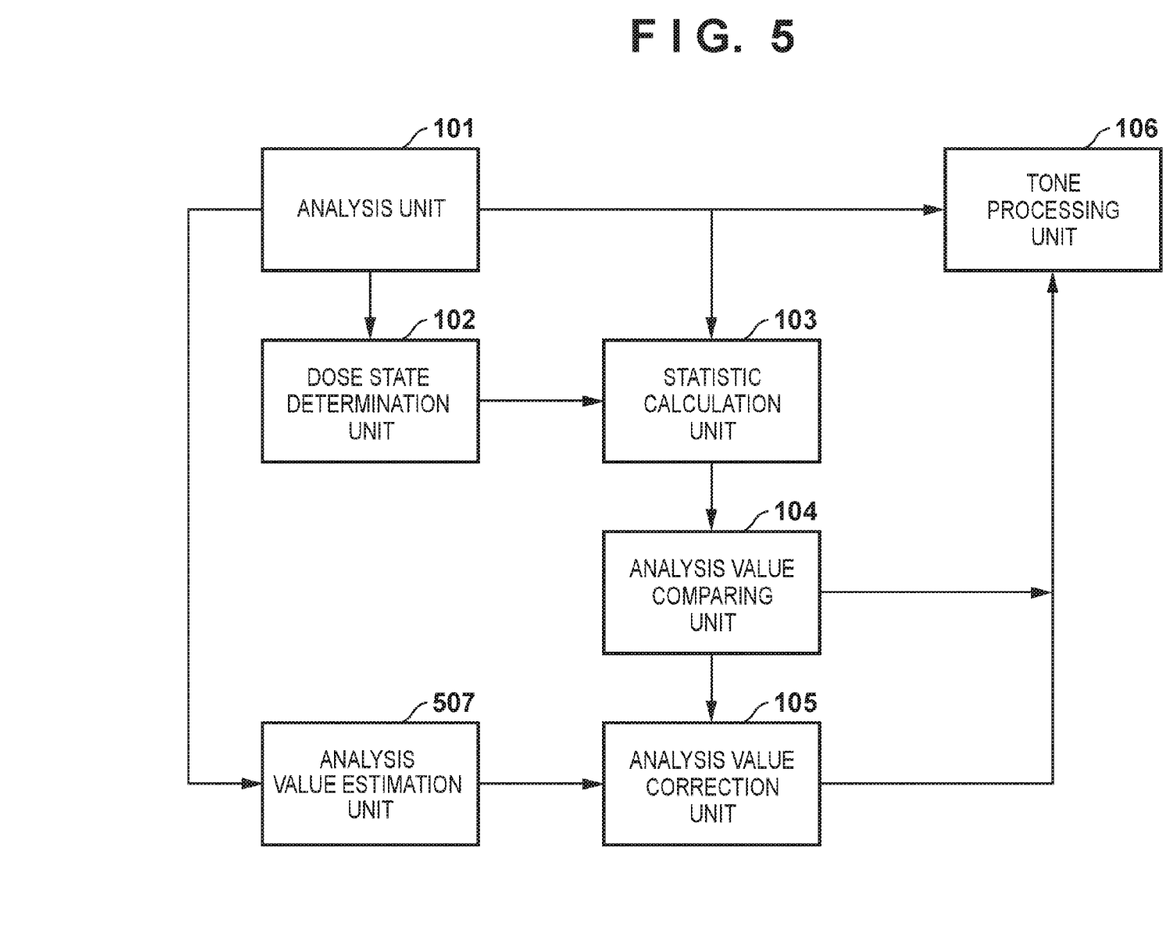
FIG. 5 is a block diagram showing an example of the functional arrangement of an X-ray image processing apparatus according to the fourth embodiment.
Figure 7:
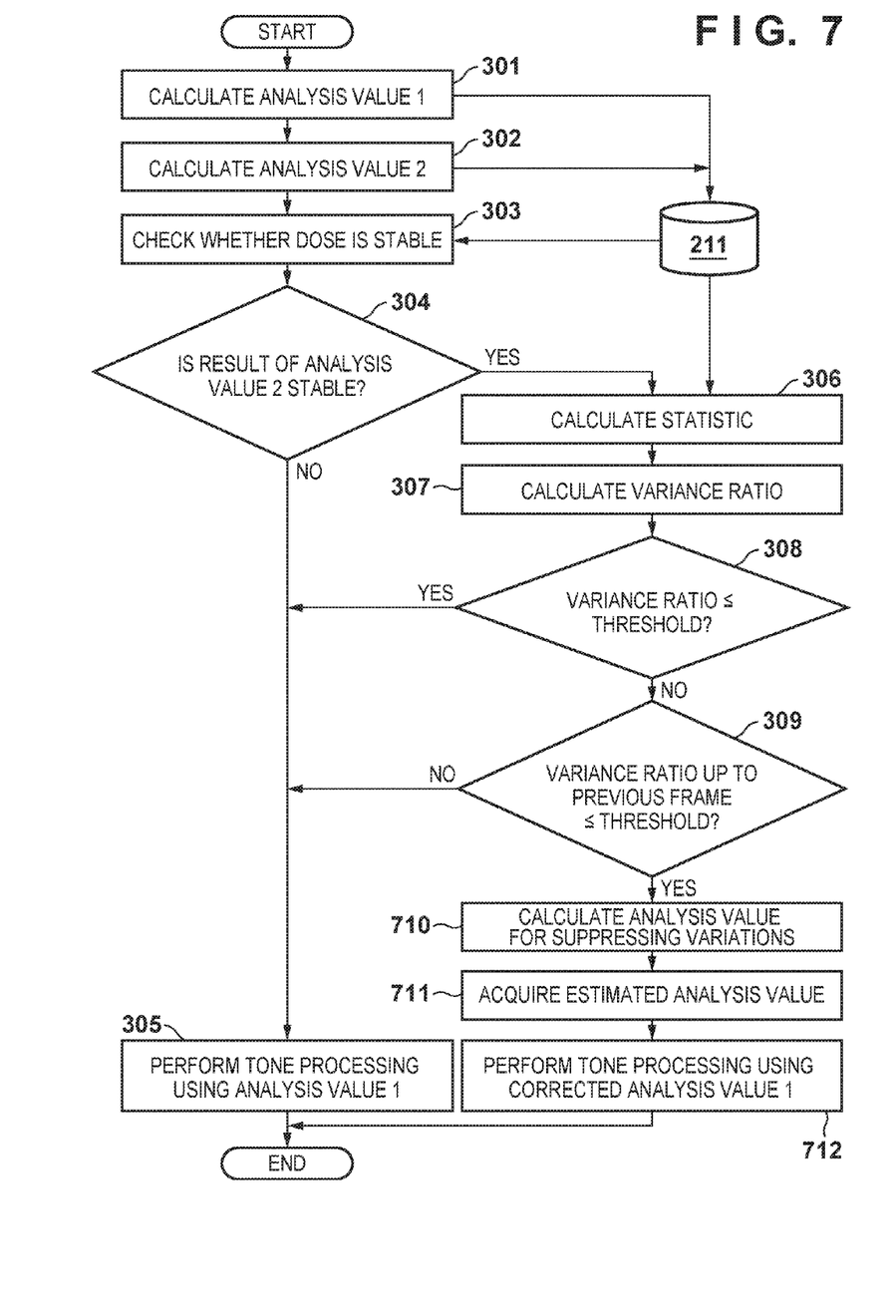
FIG. 7 is a flowchart illustrating processing of acquiring analysis values for tone processing according to the fourth embodiment.

Another example of the method of selecting one solution when the solution of the quadratic equation of analysis value 3 is a real number will be described with reference to the block diagram of FIG. 5 and the flowchart of FIG. 7. In the fourth embodiment, an estimated value (estimated analysis value) of analysis value 1 of the current frame is acquired from analysis values 1 obtained from a plurality of past frames, and a solution is selected based on the estimated analysis value. Therefore, in a functional arrangement for implementing an X-ray image processing method shown in FIG. 5, an analysis value estimation unit 507 is added to the arrangement shown in FIG. 1. The analysis value estimation unit 507 receives analysis values 1 of past frames, and outputs an estimated analysis value obtained as a result of estimating analysis value 1 of the current frame. Steps 701 to 709 are the same as steps 301 to 309 and a description thereof will be omitted.

An analysis value correction unit 105 receives analysis values 1, their variance $V_1(t)$, and a variance $V_2(t)$ of analysis values 2, and outputs analysis value 3 obtained by correcting a failed result (step 710). Analysis value 1 is corrected using equations (3) so that a variance ratio becomes equal to or smaller than a threshold thF. When the solution is a real number, two solutions ($R_{31}(t)$ and $R_{32}(t)$) are obtained.

The analysis value estimation unit 507 reads out analysis value 1 and analysis values 1 calculated in the past frames from an external storage unit 211, and outputs $R_3(t)'$ as an estimated analysis value (step 711). As a method of calculating an estimated analysis value, for example, there is a method of extrapolating analysis values 1 in the time direction using spline interpolation or the like. In this embodiment, the analysis value correction unit 105 selects one of the two analysis values obtained in step 710 by using the estimated analysis value $R_3(t)'$ (step 712) by:

$$|R_{31}(t)-R'_3(t)| \le |R_{32}(t)-R'_3(t)| \ldots R_3(t)=R_{31}(t)$$

$$|R_{31}(t)-R'_3(t)| > |R_{32}(t)-R'_3(t)| \ldots R_3(t)=R_{32}(t) \quad (7)$$

Figure 6C:
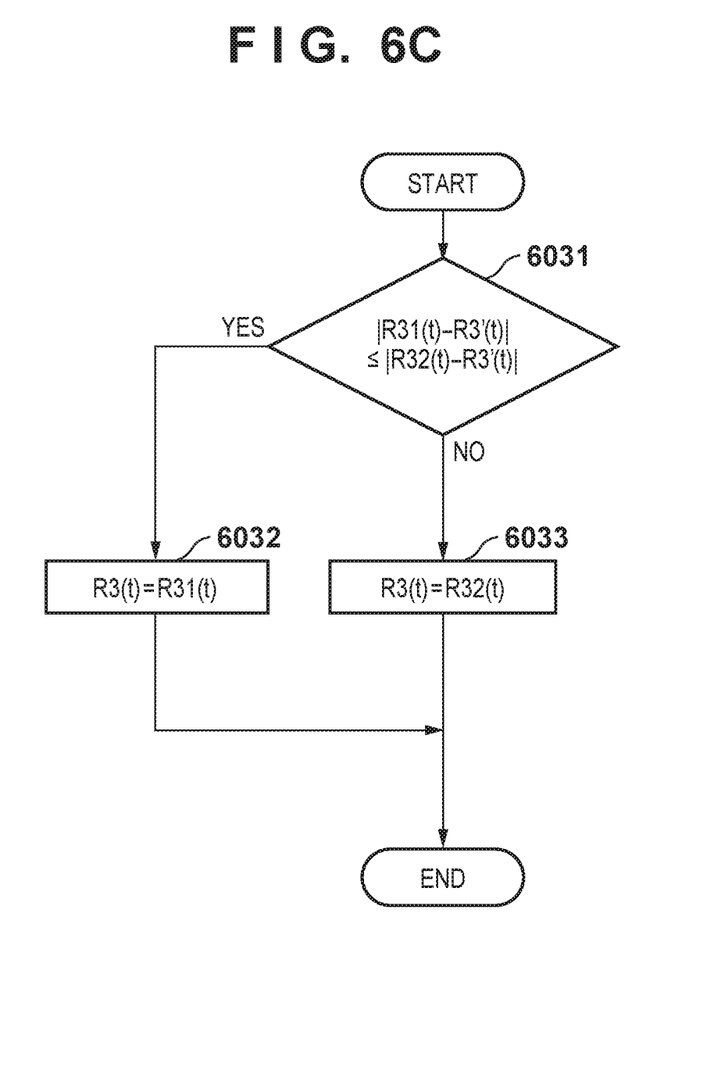
FIG. 6C is a flowchart for explaining a solution selection procedure.

That is, as shown in the flowchart of FIG. 6C, a distance between $R_3(t)'$ and each of $R_{31}(t)$ and $R_{32}(t)$ is calculated (step 6031), and a solution having a shorter distance is determined as a more optimum solution (steps 6032 and 6033).

Fifth Embodiment

Note that in the above-described first to fourth embodiments, analysis value 1 calculated as a value representing an object region is used. However, the present invention is not limited to this. For example, a result obtained by performing flicker countermeasure processing for a calculated value representing an object region may be defined as analysis value 1, and the above-described processing may be performed. In this case, as a suppression method of interpolating flicker which cannot be suppressed by known flicker countermeasure processing, it is possible to operate the processing of each of the embodiments.

Other Embodiments

The present invention is also implemented by executing the following processing. That is, software (program) for implementing the functions of the above-described embodiments is supplied to a system or apparatus via a network or various kinds of storage media, and the computer (or CPU or MPU) of the system or apparatus reads out and executes the program.

The present invention is not limited to the above embodiments and various changes and modifications can be made without departing from the spirit and scope of the present invention. Therefore, to apprise the public of the scope of the present invention, the following claims are made.

The invention claimed is:
1. An X-ray image processing apparatus for performing image processing for frames successively obtained by an X-ray sensor, comprising:
a memory storing instructions; and
one or more processors which, when executing the instructions, function as:
an analysis unit configured to obtain a first analysis value and a second analysis value by analyzing different regions in each of the successively obtained frames;
a calculation unit configured to calculate, as a first statistic and a second statistic, a variance or a standard deviation of the first analysis values and the second analysis values in the successively obtained frames;
a determination unit configured to determine, based on the first statistic and the second statistic, whether to correct the first analysis value;
a correction unit configured to, if the determination unit determines to correct the first analysis value, correct the first analysis value based on the first statistic; and a tone processing unit configured to perform tone processing on a frame of the successively obtained frames based on the corrected first analysis value.

2. The X-ray image processing apparatus according to claim 1, wherein if it is determined based on the second statistic that an X-ray dose is stable, the determination unit determines based on the first statistic and the second statistic whether to correct the first analysis value.

3. The X-ray image processing apparatus according to claim 1, wherein the analysis unit acquires the first analysis value by analyzing an object region of the frame, and obtains the second analysis value by analyzing a region of a predetermined size at a predetermined position in the frame.

4. The X-ray image processing apparatus according to claim 2, wherein if a ratio between the first statistic and the second statistic exceeds a threshold, the determination unit determines to correct the first analysis value.

5. The X-ray image processing apparatus according to claim 4, wherein the correction unit corrects the first analysis value so that the ratio becomes equal to the threshold.

6. The X-ray image processing apparatus according to claim 4, wherein the correction unit corrects the first analysis value so that the ratio becomes closest to the threshold.

7. The X-ray image processing apparatus according to claim 1, wherein the calculation unit calculates the statistic by excluding, from analysis values of past frames, an analysis value for which the determination unit determines that correction is necessary.

8. The X-ray image processing apparatus according to claim 5, wherein the correction unit outputs, as the first analysis value after correction, an analysis value having a smallest difference with respect to the first analysis value before correction among a plurality of analysis values obtained to equalize the ratio to the threshold.

9. The X-ray image processing apparatus according to claim 4, further comprising:
an estimation unit configured to acquire an estimated analysis value from the first analysis values obtained from a plurality of past frames,
wherein the correction unit outputs, as the first analysis value after correction, an analysis value having a smallest difference with respect to the analysis value estimated by the estimation unit among a plurality of analysis values obtained to equalize the ratio to the threshold.

10. The X-ray image processing apparatus according to claim 4, wherein the correction unit selects, as the first analysis value after correction, an analysis value which makes a sign of a derivative value in a time direction of the first analysis values match a sign of a derivative value in a time direction of the second analysis values among a plurality of analysis values obtained to equalize the ratio to the threshold.

11. The X-ray image processing apparatus according to claim 10, wherein the correction unit selects, as the first analysis value after correction, an analysis value having a smallest difference between the derivative value in a time direction of the first analysis values and the derivative value in a time direction of the second analysis value among a plurality of analysis values obtained to equalize the ratio to the threshold.

12. The X-ray image processing apparatus according to claim 1, wherein the memory stores further instructions, which when executed by the one or more processors, cause the image processing apparatus to function as:
a holding unit configured to hold the first analysis values of a predetermined number of past frames; and
a confirmation unit configured to confirm, based on a statistic in a time direction of the first analysis values of the predetermined number of frames, that acquisition of the first analysis value of a current frame has failed,
wherein if the confirmation unit cannot confirm that acquisition of the first analysis value of the current frame has failed, the correction unit prohibits correction of the first analysis value.

13. The X-ray image processing apparatus according to claim 12, wherein
the holding unit discards the first analysis value corresponding to a held oldest frame, and holds a newly calculated first analysis value, and
the holding unit holds no first analysis value which needs to be corrected by the correction unit.

14. The X-ray image processing apparatus according to claim 13, wherein if the number of frames between a frame corresponding to an oldest first analysis value and the current frame exceeds a predetermined number of frames, the holding unit holds the first analysis value of the current frame regardless of whether correction is necessary.

15. An X-ray image processing apparatus for performing image processing for frames successively obtained by an X-ray sensor, comprising:
a memory storing instructions; and
one or more processors which, when executing the instructions, function as:
an analysis unit configured to obtain an analysis value by analyzing different regions in each of the successively obtained frames;
a calculation unit configured to calculate a variance or standard deviation of the analysis value in a time direction of the analysis values of the successively obtained frames;
a correction unit configured to correct the analysis value based on the variance or standard deviation of the analysis value; and
a tone processing unit configured to perform tone processing on a frame of the successively obtained frames based on the corrected analysis value.

16. An X-ray image processing method of performing image processing for frames successively obtained by an X-ray sensor, the method comprising:
obtaining an analysis value by analyzing different regions in each of the successively obtained frames;
calculating a variance or standard deviation of the analysis value in a time direction of the analysis values of the successively obtained frames;
correcting the analysis value based on the variance or standard deviation of the analysis value; and
performing tone processing on a frame of the successively obtained frames based on the corrected analysis value.

17. An X-ray imaging apparatus comprising:
an X-ray sensor configured to output an electrical signal corresponding to an X-ray dose;
the X-ray image processing apparatus according to claim 15; and, further comprising
an X-ray generation apparatus configured to generate X-rays.

18. An X-ray image processing apparatus for performing image processing for frames successively obtained by an X-ray sensor, comprising:
a memory storing instructions; and
one or more processors which, when executing the instructions, function as:

an analysis unit configured to obtain a first analysis value and a second analysis value by analyzing two regions of each of the successively obtained frames;

a calculation unit configured to calculate, as a first statistic and a second statistic, a variance or standard deviation of the first analysis values and the second analysis values indicating a time variation of the first analysis values and the second analysis values of the successively obtained frames;

a determination unit configured to determine whether to correct a time variation of the first analysis value based on the first statistic and the second statistic; and a tone processing unit configured to, if the determination unit determines not to correct the time variation of the first analysis value, perform tone processing on a frame of the successively obtained frames based on the first analysis value.

19. An X-ray image processing method of performing image processing for frames successively obtained by an X-ray sensor, the method comprising:

obtaining a first analysis value and a second analysis value by analyzing two regions of each of the successively obtained frames;

calculating, as a first statistic and a second statistic, a variance or standard deviation of the first analysis values and the second analysis values indicating a time variation of the first analysis values and the second analysis values of the successively obtained frames;

determining whether to correct a time variation of the first analysis value based on the first statistic and the second statistic; and if it is determined not to correct the time variation of the first analysis value, performing tone processing on a frame of the successively obtained frames based on the first analysis value.

20. The X-ray image processing apparatus according to claim 1, wherein the one or more processors, when executing the instructions, further function as a tone processing unit configured to perform tone processing on the frame based on the corrected first analysis value.

21. The X-ray image processing apparatus according to claim 1, wherein the different regions include at least one of a collimation region or a direct irradiated region in the frame.

22. The X-ray image processing apparatus according to claim 1, wherein the first analysis value is obtained by analyzing pixel values of an object region and the second analysis value is obtained by analyzing pixel values of a predetermined region.

23. The X-ray image processing apparatus according to claim 15, wherein the analysis value is obtained by analyzing pixel values of an object region or the analysis value is obtained by analyzing pixel values of a predetermined region.

24. The X-ray image processing method according to claim 16, wherein the analysis value is obtained by analyzing pixel values of an object region or the analysis value is obtained by analyzing pixel values of a predetermined region.

25. The X-ray imaging apparatus according to claim 17, wherein the analysis value is obtained by analyzing pixel values of an object region or the analysis value is obtained by analyzing pixel values of a predetermined region.

26. The X-ray image processing apparatus according to claim 18, wherein the first analysis value is obtained by analyzing pixel values of an object region and the second analysis value is obtained by analyzing pixel values of a predetermined region.

27. The X-ray image processing method according to claim 19, wherein the first analysis value is obtained by analyzing pixel values of an object region and the second analysis value is obtained by analyzing pixel values of a predetermined region.

* * * * *